US009925289B2

(12) United States Patent
Trebbi et al.

(10) Patent No.: US 9,925,289 B2
(45) Date of Patent: Mar. 27, 2018

(54) LYOPHILIZING MACHINE COMPRISING AT LEAST A GUIDE MEMBER FOR LOADING DEVICES

(71) Applicant: I.M.A. INDUSTRIA MACCHINE AUTOMATICHE S.P.A., Ozzano Dell'Emilia (IT)

(72) Inventors: Claudio Trebbi, Medicina (IT); Gabriele Gabusi, Castenaso (IT)

(73) Assignee: I.M.A. INDUSTRIA MACCHINE AUTOMATICHE S.P.A., Ozzano Dell'Emilia (IT)

(*) Notice: Subject to any disclaimer, the term of this patent is extended or adjusted under 35 U.S.C. 154(b) by 18 days.

(21) Appl. No.: 14/916,178

(22) PCT Filed: Sep. 4, 2014

(86) PCT No.: PCT/IB2014/064253
§ 371 (c)(1),
(2) Date: Mar. 2, 2016

(87) PCT Pub. No.: WO2015/033290
PCT Pub. Date: Mar. 12, 2015

(65) Prior Publication Data
US 2016/0193376 A1 Jul. 7, 2016

(30) Foreign Application Priority Data

Sep. 4, 2013 (IT) .............................. MI2013A1447

(51) Int. Cl.
*A61L 2/00* (2006.01)
*A61L 9/00* (2006.01)
(Continued)

(52) U.S. Cl.
CPC ........ *A61L 2/26* (2013.01); *A61L 2/24* (2013.01); *F26B 5/06* (2013.01); *F26B 25/003* (2013.01)

(58) Field of Classification Search
CPC ...................................... A61L 2/00; A61L 2/18
(Continued)

(56) References Cited

U.S. PATENT DOCUMENTS

| 7,328,522 | B2 | 2/2008 | Binder | |
| 8,820,516 | B2 * | 9/2014 | Christ | F26B 5/06 198/747 |
| 2012/0186947 | A1 | 7/2012 | Christ | |

FOREIGN PATENT DOCUMENTS

| DE | 102009008970 A1 | 6/2010 |
| DE | 102011117628 A1 | 5/2013 |

(Continued)

OTHER PUBLICATIONS

European Patent Office English Translation of FR 2695329.*
Search Report and Written Opinion for PCT/IB2014/064253, dated Nov. 12, 2014.

*Primary Examiner* — Monzer R Chorbaji
(74) *Attorney, Agent, or Firm* — Marshall, Gerstein & Borun LLP

(57) ABSTRACT

A lyophilizing and/or sterilizing machine comprises a treatment chamber, a plurality of loading planes having at least one loading surface, disposed inside the treatment chamber, one overlapping the other and positionable in a desired and known manner by means of vertical tie-rods. The lyophilizing and/or sterilizing machine also comprises a movement apparatus to move containers, the content of which is to be treated in the treatment chamber. The movement apparatus comprises at least one loading/unloading device mobile on horizontal guides comprising at least one internal horizontal guide independent and autonomous from the loading planes and located in correspondence to a lateral portion of the loading planes and between the loading surface and the vertical tie-rods.

20 Claims, 6 Drawing Sheets

(51) Int. Cl.
  *B08B 3/04* (2006.01)
  *A61L 2/26* (2006.01)
  *F26B 5/06* (2006.01)
  *A61L 2/24* (2006.01)
  *F26B 25/00* (2006.01)

(58) Field of Classification Search
  USPC ......... 422/1, 292, 300, 305; 134/22.1, 104.1
  See application file for complete search history.

(56) References Cited

FOREIGN PATENT DOCUMENTS

FR          2695329  A1    3/1994
FR          2695329       * 11/1994   ............... B08B 3/02

* cited by examiner

LYOPHILIZING MACHINE COMPRISING AT LEAST A GUIDE MEMBER FOR LOADING DEVICES

FIELD OF THE INVENTION

The present invention concerns a lyophilizing and/or sterilizing machine comprising loading planes and at least a guide member to move a loading device, for example defined by one or more sliders, which positions on each occasion on the loading planes the containers whose contents are to be subjected to treatment.

In particular, the present invention concerns one or more guide members positioned inside the treatment chamber of the lyophilizing and/or sterilizing machine and having one or more accessory functions other than the linear guide function for the loading sliders.

BACKGROUND OF THE INVENTION

Movement apparatuses are known, for moving the loading planes of lyophilizing and/or sterilizing machines.

Hereafter, the reference to lyophilizing machines comprises both lyophilizing machines and sterilizing machines and combined machines.

The vertical movement of each loading plane inside the chamber is obtained with the aid of vertical tie-rods associated with at least one of the loading planes according to any known technique.

Said planes can also cooperate with possible anti-oscillation guides disposed externally to the planes.

It is known to use loading/unloading sliders, or other similar or comparable means, which move the containers from a preparation plane, disposed outside the treatment chamber, to the loading plane and vice versa.

It is also known that for the loading/unloading sliders it is preferable that suitable guide members are provided which, due to the presence of the vertical tie-rods, can either be upturned or occupy usable spaces of the loading surface of each loading plane.

Moreover, the lateral bulk created by the vertical tie-rods can limit and/or obstruct the presence of the horizontal guides, whether they are mobile or fixed on the loading plane.

One disadvantage of lyophilizing machines is that the drive power and/or command and control signals are supplied to the loading/unloading slider either by means of cables that follow the loading/unloading slider itself, or by means of instructions transmitted via ether that are received by command and control units on board the slider.

Furthermore, the power needed to drive the internal members of the loading/unloading slider, and also the means that generate the movements on each occasion connected with the functions thereof, is supplied either by cables or by accumulators on board the slider.

Another disadvantage is that the slider runs on substantially flat surfaces, which entails dangers of slipping and hence the de-synchronization of the loading/unloading slider with respect to the movement cycle of the containers, and also dangers of skidding and hence loss of perpendicularity with respect to the raceways of the parts of the slider that act on the containers.

Another disadvantage of known lyophilizing machines is that they require long down time periods for the maintenance of the loading planes, for example for cleaning them, consisting of washing and/or disinfecting the relative surfaces.

Such cleaning is generally carried out from outside the treatment chamber, typically one plane at a time.

Cleaning is normally performed by an operator, using jets of water or water mixed with cleaning substances or other products, and also possibly with the aid of brushes or other cleaning instruments.

Cleaning the loading planes, which must necessarily be precise and must take place with the lyophilizing machine switched off, entails suspending the activity of the lyophilizing machine, with a consequent increase in the work times and costs.

Furthermore, manual cleaning as described above may not be accurate enough since it is difficult for the operator to reach some zones of the loading planes.

A first purpose of the present invention is to supply the necessary power and/or instructions to the loading/unloading slider from outside.

Another purpose is to control the position of the loading/unloading slider inside the treatment chamber.

Another purpose of the present invention is to obtain a lyophilizing machine comprising at least an independent horizontal guide for loading sliders, which allows to contain the cleaning times of the loading planes, consequently reducing the cycle times and work costs, and which has improved productivity and quality over known lyophilizing machines.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a lyophilizing machine according to the present invention, which overcomes the limits of the state of the art and eliminates the defects present therein, comprises a movement apparatus cooperating with a treatment chamber of the lyophilizing machine configured to move containers whose content is to be treated.

The apparatus to move the containers comprises at least a guide member, or horizontal guide, to move a loading/unloading device or slider, able to transfer the containers on the loading planes, from outside to inside and vice versa of the treatment chamber.

The loading/unloading device or slider or other mean suitable to load and unload the containers according to the invention is driven by an electric motor or a magnetic linear motor, that is, with members that generate the desired motion fed by electric current or magnetic forces.

In one solution according to the invention, a lyophilizing machine comprises, inside the treatment chamber, one or more guide members for a loading/unloading slider disposed at the sides of the loading surface of each loading plane. The guide members, or internal horizontal guides, are independent of the loading plane and substantially do not interfere either with the usable loading surface or the vertical displacement movement thereof.

Furthermore, the guide means allow the loading/unloading slider not to interfere with the vertical tie-rods that serve to position the loading planes in a known manner.

It is quite obvious that the at least one horizontal guide must be mating so as to cooperate with the loading/unloading slider.

Each horizontal guide has a stable sliding plane, defined or definable on each occasion as desired, per se or in relation to the loading plane/planes.

According to the invention, in association with the internal horizontal guides there are means of defined connection with the wheels or tracks, or other type of mean that allows the loading/unloading slider to translate so that it does not lose its synchronism in the movement cycle of the containers, nor its own perpendicularity.

According to another feature of the invention, in cooperation with the internal horizontal guides and below their upper surface, which defines the sliding surface of the loading/unloading slider there are conductor and/or signal receiver elements, suitable to put a central management, command and control unit of the lyophilizing machine in a condition of dialog with a command and control unit on board the slider.

According to another feature of the invention, again in cooperation with the sliding surfaces of the internal horizontal guides, there are energy conductors suitable to transfer the drive and operating force necessary to receiver means present in the loading/unloading slider.

According to a characteristic feature of the present invention, the treatment chamber comprises washing means associated with the at least one horizontal guide and configured to carry out at least the surface cleaning of one or more of the loading planes.

The integration in the horizontal guides according to the invention has the advantage that it allows to keep free the upper surfaces of the internal horizontal guides, where the loading/unloading slider runs. Furthermore, the invention makes cleaning easier and allows to prevent possible contamination of the treatment chamber due to the permanence of residual dirt or washing fluids.

According to the invention, washing can be automatic, programmable or semi-automatic controlled by an operator.

In particular, according to the invention, the washing means are integrated in the at least one horizontal guide, and are at least partly contained therein, and comprise at least one or more devices to deliver washing fluids and an apparatus to distribute the washing fluids.

In this way it is possible to clean at least one loading plane at a time, operating directly from inside the treatment chamber with means provided therein and in a desired manner, making the relative operations independent of the times of manual execution by an operator.

Using washing means according to the invention allows to contain said execution times, and therefore allows to reduce the overall cycle times of the lyophilizing machine. It is therefore possible to increase productivity and reduce treatment costs compared to the state of the art.

The positioning of the washing means inside the treatment chamber also has the advantage of guaranteeing a quicker, more efficient, more thorough and more uniform cleaning of the surfaces of the loading planes themselves, and possibly of every other component in the treatment chamber.

The washing fluid delivery devices comprise washing nozzles associated, according to the functions, to the horizontal guide.

The washing nozzles can be fixed or mobile, and can be configured to assume an inactive position and a work position.

The washing nozzles are associated with an apparatus to distribute washing fluids.

The distribution apparatus comprises at least a central unit, such as an accumulation tank and/or a network to distribute one or more fluids that feeds the washing nozzles in a desired manner.

The washing fluids are suitable to obtain the desired cleaning and/or disinfection of the loading planes.

According to the invention, the central unit can be connected to and commanded by a command module configured to manage and control, possibly also in feedback, all or some of the washing functions.

According to the invention, the at least one horizontal guide can be provided with position sensors, cooperating with the loading planes and possibly with a corresponding apparatus to move the loading planes in order to determine the desired reciprocal positioning of the upper surface of the loading plane to be loaded and the upper surface of the horizontal guide, both during the loading/unloading step and also, possibly, in the washing step.

In a variant, the loading planes are also provided with position sensors, which cooperate with the horizontal guide to determine their desired correct position on each occasion.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF SOME FORMS OF EMBODIMENT

Figure 1:
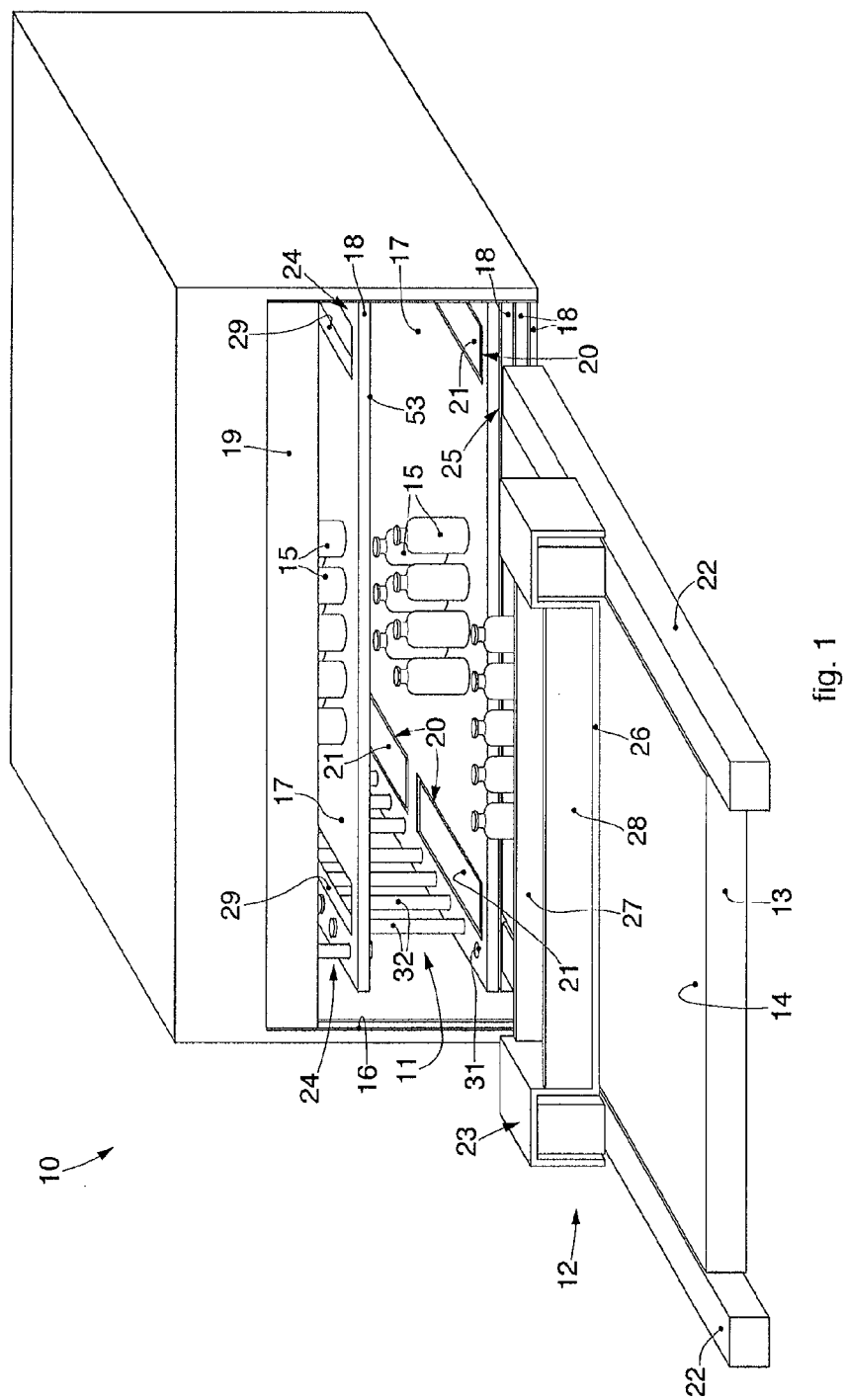
FIG. 1 is a schematic three-dimensional view of a part of a lyophilizing machine according to the present invention.
Figure 2:
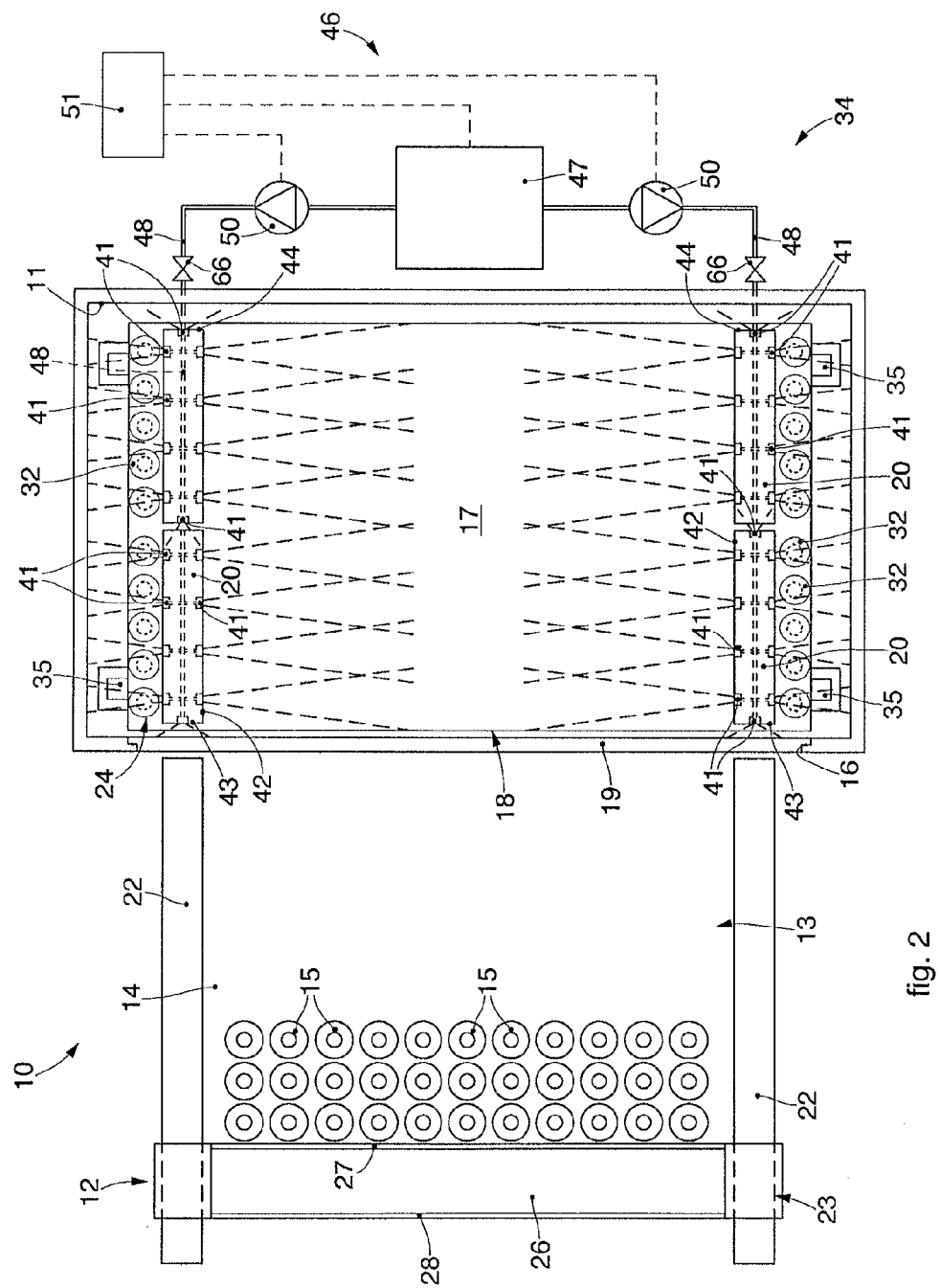
FIG. 2 is a schematic plan view of FIG. 1.

With reference to FIGS. 1 and 2, a lyophilizing machine 10 according to the present invention comprises at least a treatment chamber 11 and a movement apparatus 12 cooperating with the treatment chamber 11.

The lyophilizing machine 10 can also include a preparation plane 13, on the upper surface 14 of which containers 15 are sent and positioned, in a known manner, to be then sent to the treatment chamber 11 to be subjected to the desired treatment, from which treatment chamber 11 they are then removed, returned to the preparation plane 13 and finally distanced.

The lyophilizing machine 10 can include a plurality of loading planes 18, which are aligned in succession to the preparation plane 13 so that an upper surface thereof, or loading surface 17, can cooperate in a desired and controlled manner both with the upper surface 14 of the preparation plane 13 and also with an upper surface 21 of one or more guide members, or internal horizontal guides 20, positioned inside the treatment chamber 11.

The internal horizontal guides 20 are configured to be independent from the loading planes 18, that is, substantially not interfering either with their loading surface 17 or with the movement thereof.

In the loading step, in a known manner, the containers 15 are thrust, passing through a loading door 16, from the upper surface 14 of the preparation plane 13 to the loading surface 17 of a loading plane 18 of the treatment chamber 11.

During unloading, the containers 15 are thrust, passing through the loading door 16, from the loading surface 17 of the loading plane 18 aligned with the preparation plane 13 to the upper surface 14 of the latter.

A sealing door 19 is provided to seal the treatment chamber 11 during treatment.

In a possible implementation, the treatment chamber 11 can include continuous anti-oscillation rods 35, provided at the side of the loading planes 18.

Each loading plane 18 can include, as well as the loading surface 17, one or more through seatings 29 cooperating freely with the internal horizontal guides 20, in this specific case four.

The through seatings 29, and hence the internal horizontal guides 20, are located between the loading surface 17 and a lateral portion 24 of the loading plane 18 that serves to position, in a desired and coordinated manner, vertical guide means, for example vertical tie-rods 32. Outside the lateral portion 24 there can be positioning means for the anti-oscillation guides 35.

In the example shown here, since five loading planes 18 are provided, each loading plane 18 comprises in every respective lateral portion 24 suitable groups of five through holes 31, which serve to position and guide the vertical tie-rods 32.

FIGS. 1 and 2 are used to describe example forms of embodiment to improve the comprehension of the invention.

The internal horizontal guides 20 cooperate freely with the through seatings 29, and the internal horizontal guides 20 have an upper surface 21 that cooperates on each occasion with horizontal guides 22 outside the treatment chamber 11.

The loading/unloading device, in this specific case a loading/unloading slider 23 or other similar mean, moves on the horizontal guides 20 and 22 to perform the loading and unloading steps of the containers 15 as described above.

The resulting configuration allows the loading/unloading slider 23 or other similar mean to move freely along the internal horizontal guides 20, without problems of interference with the vertical tie-rods 32.

In the case shown here, between the internal horizontal guides 20 and the external horizontal guides 22, by way of example, there are intermediate spaces 25 which, during the loading and unloading of the containers 15, are occupied in a known manner to allow the loading/unloading slider 23 to transit and allow the sealing door 19 to seal the loading door 16.

In this specific case given by way of example, the loading/unloading slider 23 comprises a bearing structure consisting of a base 26, possibly positionable vertically, and in this specific case of two thrust walls, fixed or positionable vertically, respectively a front vertical wall 27 and a rear vertical wall 28. The thrust walls 27, 28 are able to thrust the containers 15 into or from the treatment chamber 11 during the loading and unloading steps.

Figure 3A:
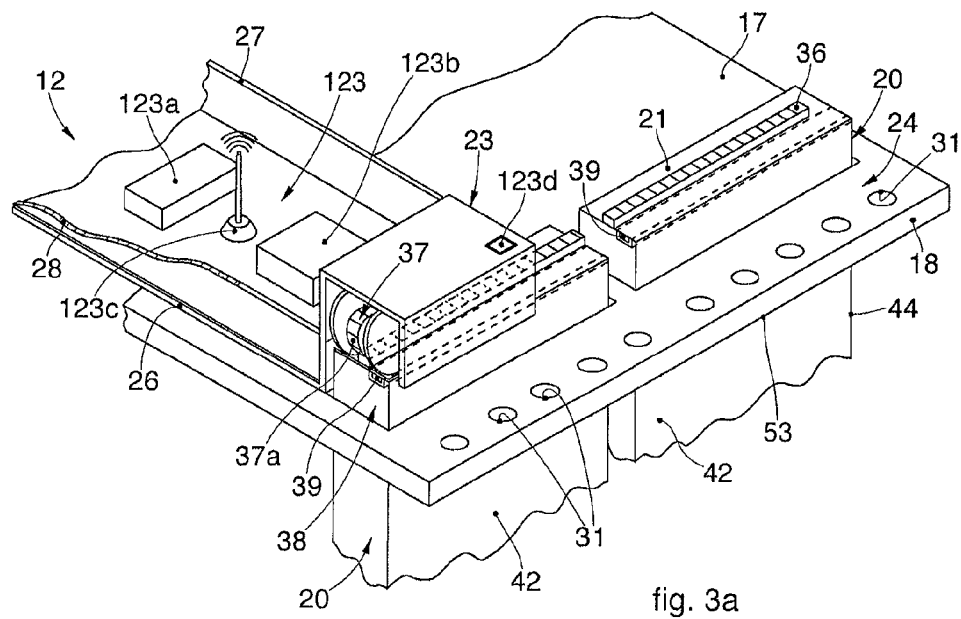
FIGS. 3a and 3b are enlargements of a detail of FIG. 1, in two variant forms.
Figure 3B:
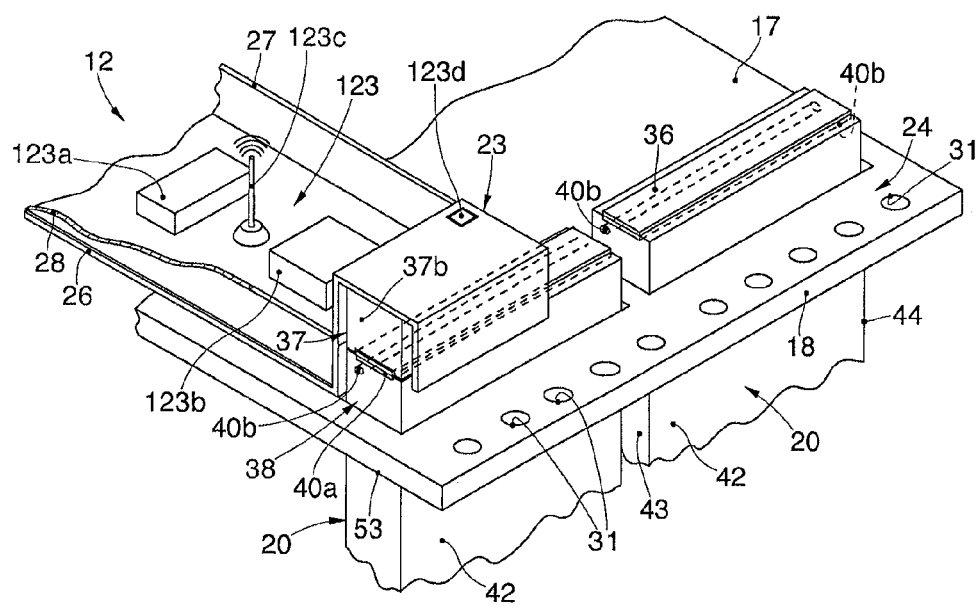

With reference to FIGS. 2, 3a and 3b, the through seatings 29 are by way of example rectangular in shape and, in this specific case, two on every side. This conformation is purely by way of example, so that the through seatings 29 can have any shape whatsoever, provided it is suitable to cooperate with the internal horizontal guides 20, thus allowing the loading planes 18 to be positioned freely at least with respect to the loading/unloading position.

The internal horizontal guides 20 can be attached to the floor or anchored for example to the structure of the treatment chamber 11, so as to position their upper surfaces 21 always aligned reciprocally, and always in the same desired position during loading/unloading and/or washing.

In this position, during the loading/unloading steps, the upper surfaces 21 of the guides can be coplanar with the loading surface 17, or can protrude from the upper part thereof (FIGS. 3a and 3b).

Figure 7:
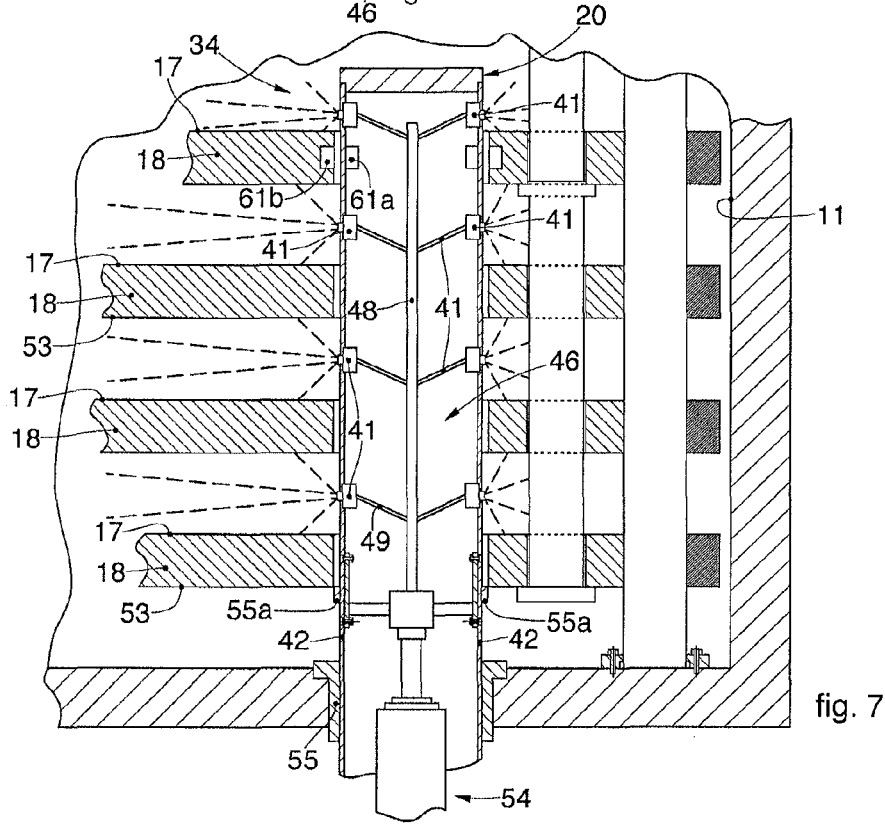

In some forms of embodiment, shown by way of example in FIG. 7, the internal horizontal guides 20 can be mobile vertically with respect to the structure of the treatment chamber 11, so as to position the upper surface 21 in the desired position on each occasion.

Depending on the specific solutions, the loading position can provide that the loading surface 17 and the upper surface 21 are coplanar, or lie at different heights.

FIGS. 3a and 3b are used to describe possible forms of embodiment according to the invention.

These forms of embodiment can provide that a segment of a raceway 36 is associated with each upper surface 21 of the internal horizontal guides 20. A drive member 37 slides along the segment of the raceway 36 and functions as a movement mean for the loading/unloading slider 23 of the movement apparatus 12.

The association of the raceway 36 and the upper surfaces 21 can provide that the segments of the former rest on the latter, and can also be attached thereto, or that they are integrated and at least partly positioned below them.

By way of example of possible forms of embodiment of the invention, FIGS. 3a and 3b show, integrated in the internal horizontal guides 20, energy supply means, for example electric energy, and/or means to transmit command and/or control signals, possibly also in feedback, which are indicated in their entirety by the reference number 38.

The supply and/or signal transmission means 38 can be, for example, electric conductors, and can be governed by one or more drive members 37, and also by command and control means 123 present on board the loading/unloading slider 23.

Between the command and control means 123 may be included, by way of example, a control unit 123a, possible accumulators or batteries 123b and communication means 123c, for example wireless, such as for example infrared, radio waves according to any of the known protocols (Wi-fi, Bluetooth, Zig-bee, etc.), or laser beam. Possible position control devices 123d to control and verify the position of the one or more drive members 37 and/or the positioning of one or both the thrust walls 27, 28 of the loading/unloading slider 23 can be provided in cooperation both with the supply and/or signal transmission means 38 integrated in the internal horizontal guides 20, and also with the control unit 123a on board the loading/unloading slider 23.

The position control devices 123d and the supply and/or signal transmission means 38 can allow the control unit 123a to act, possibly in feedback, on the one or more drive members 37, to position the loading/unloading slider 23 in the desired position of alignment and to compensate for possible skidding and misalignments.

FIG. 3a shows an example where the drive member 37 for moving the loading/unloading slider 23 includes a track 37a which cooperates with the raceway 36 which, in this specific case, is the rack type.

In the forms of embodiment described with reference to FIG. 3a, the supply and/or signal transmission means 38 can be associated in a single electric conductor 39, integrated in the internal horizontal guide 20.

The single electric conductor 39 is configured both to supply power to the movement track 37a of the loading/unloading slider 23, and also possibly to transmit to and receive from the latter command and/or control signals and information. The exchange of the command and/or control signals and information can occur toward one or all the command and control means 123 of the loading/unloading slider 23.

Advantageously, in the case shown by way of example with reference to FIG. 3*a*, the single electric conductor 39 is located below the upper surface 21 of the internal horizontal guide 20, so as to isolate it more from the latter and to keep the upper surface 21 where the loading/unloading slider 23 slides as free as possible.

The single electric conductor 39 can be connected, in a known manner, with energy captation elements, not shown in the drawings, which in turn are connected to the track 37*a* and to one or more of the command and control means 123 on board the loading/unloading slider 23 to supply them with the electric energy captured.

FIG. 3*b* shows an example where the drive member 37 of the loading/unloading slider 23 includes the active part 37*b* of a linear motor that cooperates with the raceway 36, which defines the passive part of the linear motor.

The sole purpose of the passive part is to prevent there being, inside the treatment chamber 11, any magnetic sources during the treatment step.

A first electric conductor 40*a*, configured to supply power to the raceway 36 and possibly also to the active part 37*b*, is integrated in the internal horizontal guide 20 shown in FIG. 3*b*.

In this specific case, the first electric conductor 40*a* can be located below the raceway 36 and, in possible advantageous formulations, can be positioned in the internal horizontal guide 20 below the upper surface 21 of the latter.

In the same way as described above, in possible implementations the first electric conductor 40*a* can be connected to one or more of the command and control means 123 to supply them with energy, for example electric power. Moreover, by way of example, a second electric conductor 40*b* is provided, integrated in the internal horizontal guide 20 and isolated therefrom, configured to transmit signals and information to and from the loading/unloading slider 23, for example at least to the control unit 123*a* located on board the loading/unloading slider 23.

In possible forms of embodiment of the present invention, the second electric conductor 40*b* can also be positioned below the upper surface 21 of the internal horizontal guide 20.

With reference to the attached drawings, by way of example, each internal horizontal guide 20 is box-shaped, where lateral walls 42, a front wall 43 facing toward the loading door 16, and a rear wall 44 facing toward the bottom of the treatment chamber 11, delimit an internal compartment 45.

What is described here refers to this conformation of the internal horizontal guides 20 only by way of example, but can easily be adapted by the person of skill to other conformations of the internal horizontal guides 20, for example where they are defined by a single block, worked to make housing seatings or internal compartments therefrom. The single block can be made of metal or plastic and can have, for example, in the zone where the loading/unloading slider 23 transits, means with high resistance to wear, such as metal, ceramic, plastic materials or particular composites.

The lyophilizing machine 10 according to the invention includes washing means 34, associated with the internal horizontal guides 20 and the loading planes 18 so as to carry out cleaning thereof.

FIG. 2 shows by way of example internal horizontal guides 20 each of which includes a plurality of washing nozzles 41 that act as devices to deliver washing fluids to at least one loading plane 18 so as to clean at least most of the surfaces thereof.

In FIG. 2, at least some of the washing nozzles 41 are associated with the lateral walls 42 of the internal horizontal guides 20 and deliver the washing fluids at least on the loading surface 17.

In the same drawing, the internal horizontal guides 20 nearest the loading door 16 include a washing nozzle 41 associated with the front wall 43, while one washing nozzle 41 is associated with the rear wall 44 of the two internal horizontal guides 20 nearest the bottom of the treatment chamber 11.

Washing nozzles 41 can also be provided to cooperate with the front walls 43 and/or reciprocally facing rear walls 44 in each pair of internal horizontal guides 20.

The washing nozzles 41 can be chosen, both as type and as number, and sized so as to deliver jets of different power, shape and size, depending on the result desired.

In FIG. 2, the washing nozzles 41 are disposed so as to cover with their jets the totality of the loading surface 17.

The jets delivered by the washing nozzles 41 can be blade type, with a full or hollow cone, with a circular or oval impression, with a symmetrical or asymmetrical impression, fixed or rotary.

The washing nozzles 41 can all be the same or different depending on the position along the corresponding internal horizontal guide 20.

The washing nozzles 41 can be configured for the exclusive delivery of liquids, of various type and/or density, or for exclusive delivery of gaseous fluids, or for the combined delivery of both liquids and gaseous fluids, pre-mixed: the products delivered can be either cold or hot.

In some forms of embodiment, the washing means 34 that the lyophilizing machine 10 is provided with include a distribution apparatus 46, the function of which is to distribute the washing fluids to the washing nozzles 41.

In one possible form of embodiment, the washing means 34 include the washing nozzles 41, feed channels 49 to feed the washing fluids to the washing nozzles 41, interception and/or selection means, such as interception valves 66 and/or selection valves 65, possible delivery pumps 50, an accumulation tank 47, and also devices to discharge used fluids 59, 60, and a possible command module 51.

The accumulation tank 47 can also be a normal water supply system, a steam system, or other types of apparatuses to contain and/or distribute substances useful for cleaning or drying surfaces.

The accumulation tank 47 is connected to the washing nozzles 41 by means of collectors 48 of various shape.

In the example, a collector 48 feeds distribution pipes 49 that carry the washing fluids to one or more washing nozzles 41.

The distribution pipes 49 are shown by way of example inclined so as to discharge the excess liquid into the collector 48, to prevent there being any cleaning liquids present in the treatment chamber 11 during treatment.

According to the invention, in proximity to the washing nozzles 41 and associated with each distribution pipe 49 a device may be provided to blow in filtered air under pressure (not shown in the drawings), the purpose of which is to totally eliminate the washing fluids both from the washing nozzles 41 and also from the internal compartment 45 of the corresponding internal horizontal guide 20, and consequently from the treatment chamber 11.

In possible implementations, the distribution pipes 49 can be connected directly and independently to the accumulation tank 47, without interposition of the collectors 48.

The distribution apparatus 46 can also include one or more pumping devices, such as delivery pumps 50, which allow to send the washing fluids from the accumulation tank 47 to the washing nozzles 41 with a desired pressure.

In the forms of embodiment described here, as interception and/or selection device, one or more interception valves 66 may be provided, cooperating with one collector 48 or with all the collectors 48, positioned upstream of the treatment chamber 11 and configured to isolate hydraulically the treatment chamber 11 from the distribution apparatus 46 during the treatment steps, and to allow the washing fluids to flow to the treatment chamber 11 during the operations to clean the loading planes 18.

With reference to FIG. 2, the command module 51, if provided, is connected to the accumulation tank 47 and possible delivery pumps 50, and also to the one or more interception valves 66, to manage the cleaning activity as desired.

FIGS. 4 to 9 show, for graphical clarity, only one of the internal horizontal guides 20, in section and enlarged, and the part of the corresponding treatment chamber 11. Hereafter in the description, the reference to an internal horizontal guide 20 will only have value as one example of the solutions that can be adopted for all the internal horizontal guides 20 present in the treatment chamber 11.

Figure 4:
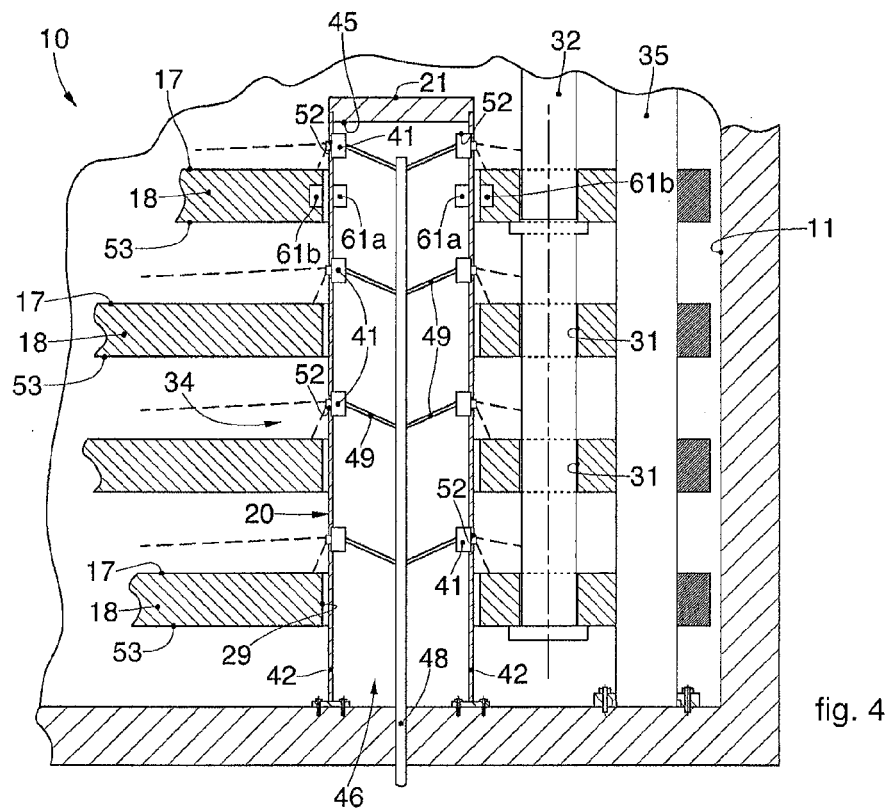
FIGS. 4 to 8 are part views, in section, of a detail of FIG. 1, according to different forms of embodiment.

In FIG. 4, the internal horizontal guide 20 is anchored to the floor and includes, inside its internal compartment 45, a part of the collector 48, from which branch off distribution pipes 49 which have an equal number of washing nozzles 41 as their terminals.

The washing nozzles 41, and consequently the distribution pipes 49, are disposed in this specific case horizontally on four rows, overlapping vertically, in each lateral wall 42 of the internal horizontal guide 20.

The rows of washing nozzles 41 of one lateral wall 42 can be, as in FIG. 4, aligned horizontally with those of the opposite lateral wall 42, on planes parallel to the loading surface 17.

In this way it is possible to simultaneously clean both the part of the loading plane 18 comprised between the internal horizontal guides 20, and also the part of the loading plane 18 defined by the lateral portions 24.

Each washing nozzle 41 is housed, in this specific case partly, in a housing seating 52 made in the lateral wall 42 of the internal horizontal guide 20 and open toward the outside of the latter.

This arrangement of the washing nozzles 41 can be provided for the simultaneous cleaning of the loading surfaces 17 of four loading planes 18, that is, as many loading planes as there are pairs of opposite rows of washing nozzles 41.

The simultaneous cleaning of loading planes 18 in groups can also be associated with a movement of the loading planes 18 and a reciprocally separated arrangement thereof, so as to allow the delivery of the washing fluids in the interspaces which are thus created.

Steam can also be delivered from the washing nozzles 41, for example, with a sterilizing and drying function.

It is clear from the above that in simplified forms of embodiment, in which a single pair of opposite rows of washing nozzles 41 is provided, a single loading plane 18 can be cleaned at a time.

Figure 5:
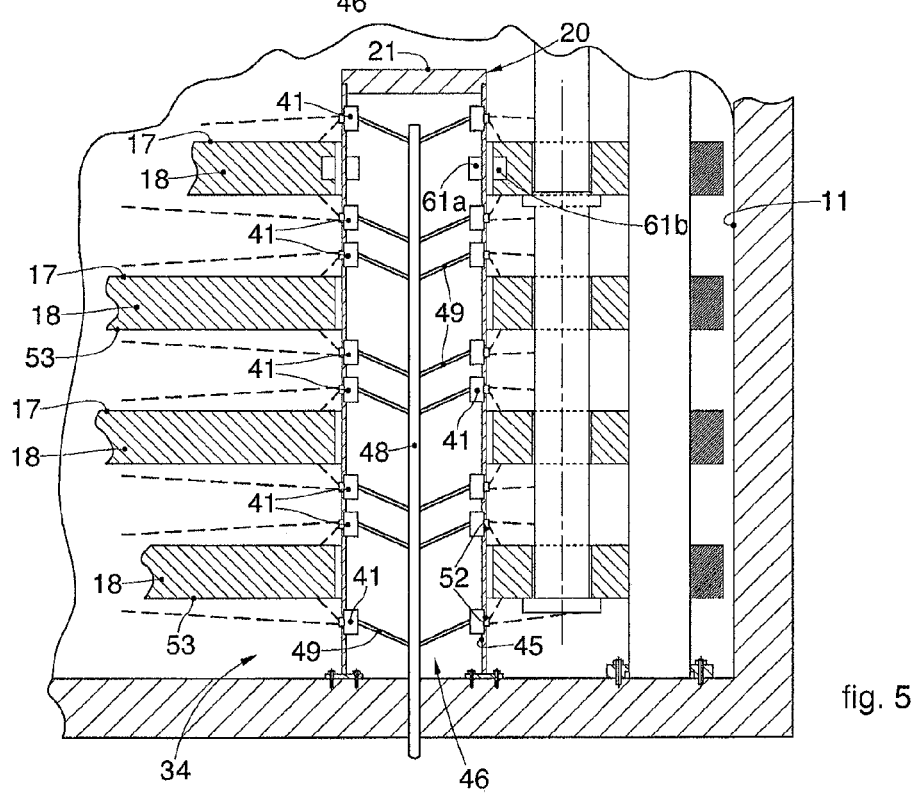

FIG. 5 is used to describe a possible variant of FIG. 4 in which the washing nozzles 41 are disposed on eight pairs of opposite rows on the two lateral walls 42 of the internal horizontal guide 20.

There are also eight pairs of rows of distribution pipes 49 and a collector 48.

The rows of washing nozzles 41 of each lateral wall 42 can be alternated, so that one row provides to clean the loading surface 17 of one loading plane 18, while the row below provides, at the same time, to clean the lower surface 53 of the latter.

This solution allows to further speed up the cleaning times of the loading planes 18 and is preferable when there is a large number of loading planes 18.

Figure 6:
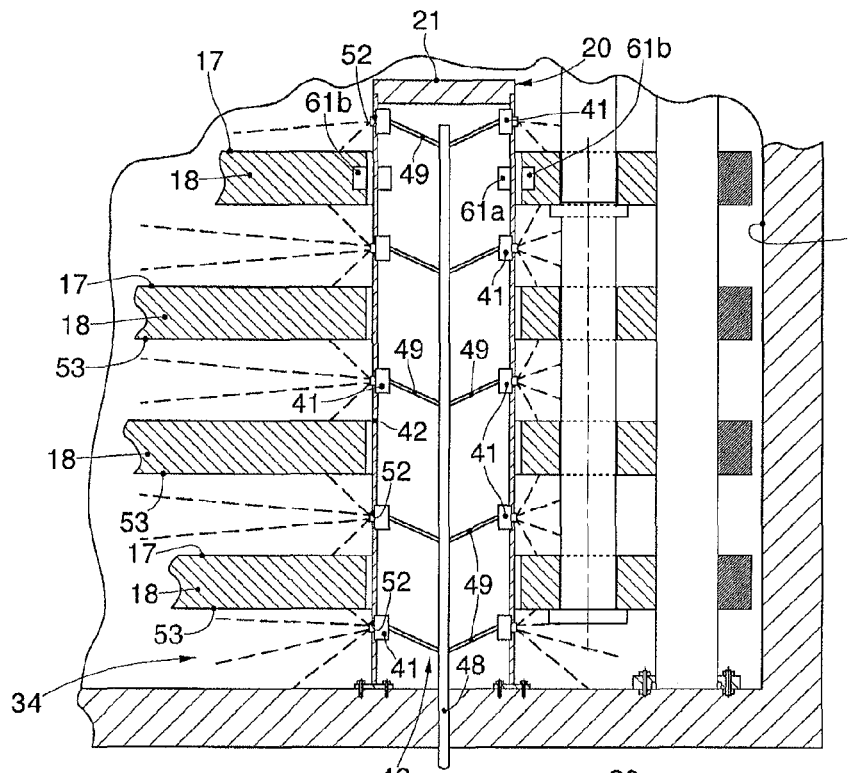

FIG. 6 shows an example of a form of embodiment in which the washing nozzles 41 are disposed on four pairs of opposite rows on the lateral walls 42 of the internal horizontal guide 20 and are configured to each deliver washing fluids both on the loading surface 17 of one loading plane 18 and also on the lower surface 53 of the loading plane 18 above.

FIG. 7 is used to describe forms of embodiment in which the internal horizontal guide 20 is not anchored to the floor or base of the treatment chamber 11, as in the variants in FIGS. 4 and 5, but is connected to a lifting device 54.

The lifting device 54 can be a mechanical, pneumatic or hydraulic linear actuator, such as for example a piston or screw jack, or any other type of actuator suitable for the purpose.

The lifting device 54 can have both the function of allowing a desired positioning of the upper surface 21 of the internal horizontal guide 20 for the loading/unloading steps, for example modifying the height thereof according to the configuration of the loading/unloading slider 23, and also, possibly, the function of allowing to move the internal horizontal guide 20 during the cleaning of the loading planes 18.

In fact, when the number of the loading planes 18 is such that too many rows of washing nozzles 41 would be needed compared with those actually housable in the walls of the internal horizontal guide 20, it is possible to clean one or a group of loading planes 18 at a time, moving the internal horizontal guide 20 to successive heights corresponding to the height of the loading plane 18 or group of loading planes 18 to be cleaned.

One example of this cleaning process may provide to position the internal horizontal guide 20 at maximum height, extending the lifting device 54 to its maximum, to carry out a first cleaning of one or a group of loading planes 18, after which it is moved to a lower height, retracting the internal horizontal guide 20 inside a sliding seating 55 thereof.

When all the loading planes 18 have been cleaned, the internal horizontal guide 20 can be positioned in its work condition, at end-of-travel inside the sliding seating 55. In this position, sealing means 55a of the internal horizontal guide 20 cooperate with the sliding seating 55 to guarantee the seal thereof during the lyophilizing/sterilizing cycles.

Figure 8:
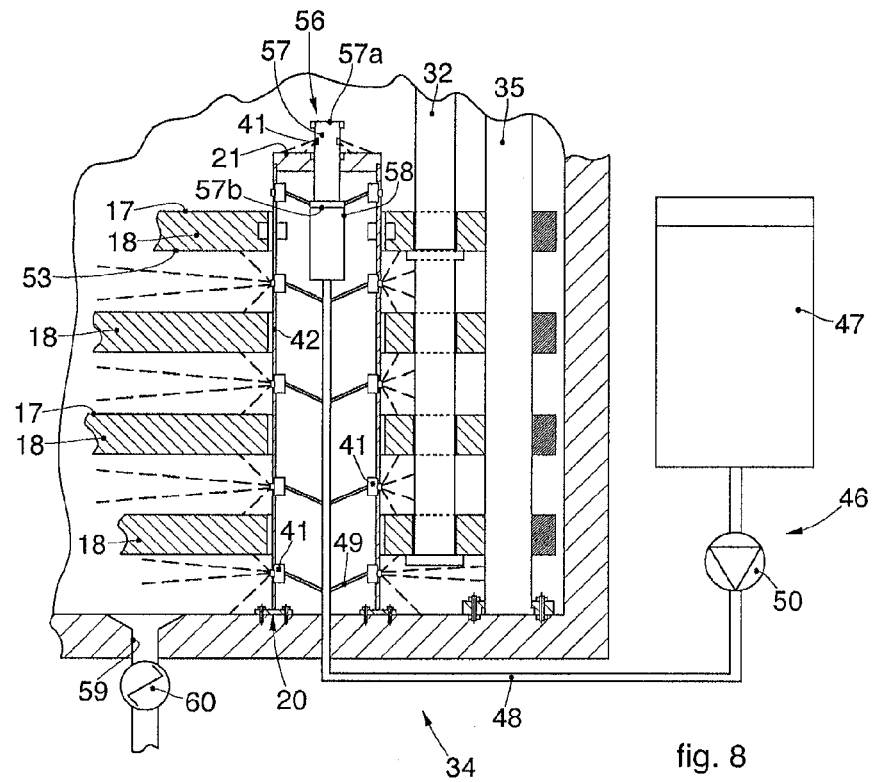

FIG. 8 is used to describe other possible forms of embodiment, which can be combined with the forms of embodiment described above, in which the washing means also include a guide washing device 56, integrated in the internal horizontal guide 20 and configured to carry out the cleaning of the upper surface 21.

The guide washing device 56 can be completely or partly contained inside a housing seating 52a made in the upper part of the internal horizontal guide 20 and communicating with the outside through the upper surface 21.

The guide washing device 56 can be the retractable type and, by way of example, include a piston 57 sliding inside a cylinder 58.

The piston 57 can in turn include one or more washing nozzles 41 configured to wash the upper surface 21 of the internal horizontal guide 20.

In the inactive condition, the piston 57 is completely inside the internal horizontal guide 20 and a top surface 57*a* thereof is substantially aligned with the upper surface 21 of the internal horizontal guide 20.

The cylinder 58 can be connected to the collector 48 and receive therefrom washing fluids that hit against a thrust surface 57*b* of the piston 57, opposite the top surface 57*a*.

The washing fluids are put under pressure by the delivery pump 50 interposed between the central unit 47 and the collector 48.

In the example shown, due to their pressure, the washing fluids thrust the piston 57 toward the outside of the cylinder 58. The piston 57 partly exits from the cylinder 58, lifting itself from the surface 21 of the internal horizontal guide 20 by a quantity such as to allow the positioning of the washing nozzles 41 at a desired distance therefrom.

When the piston 57 is in the extracted position, the washing nozzles 41 are able to deliver the washing fluids onto the surface 21 of the internal horizontal guide 20.

FIG. 8 can also be used to describe forms of embodiment in which the lyophilizing machine 10, on the base of its treatment chamber 11, includes a discharge pipe 59, the opening and closing of which can be managed by a shutter valve 60, for example the ball type, commanded by the command module 51.

Advantageously, it can also be provided that the base of the treatment chamber 11 is inclined, with an inclination converging toward the discharge pipe 59.

FIGS. 4 to 9 show, by way of example, first position sensors 61*a*, connected to the upper part of the internal horizontal guide 20, and second position sensors 61*b*, associated with the loading planes 18 and positioned on one or more of the walls that delimit the through seatings 29.

The second position sensors 61*b* can be aligned with, or facing, the first position sensors 61*a*, so that the current position of the internal horizontal guide 20 and/or the loading plane 18 to which they are associated can be known at every moment.

This allows to position the loading planes 18 always correctly during the loading/unloading operations, and also the internal horizontal guides 20, reciprocally to the loading planes 18, during the surface maintenance of the latter.

Figure 9:
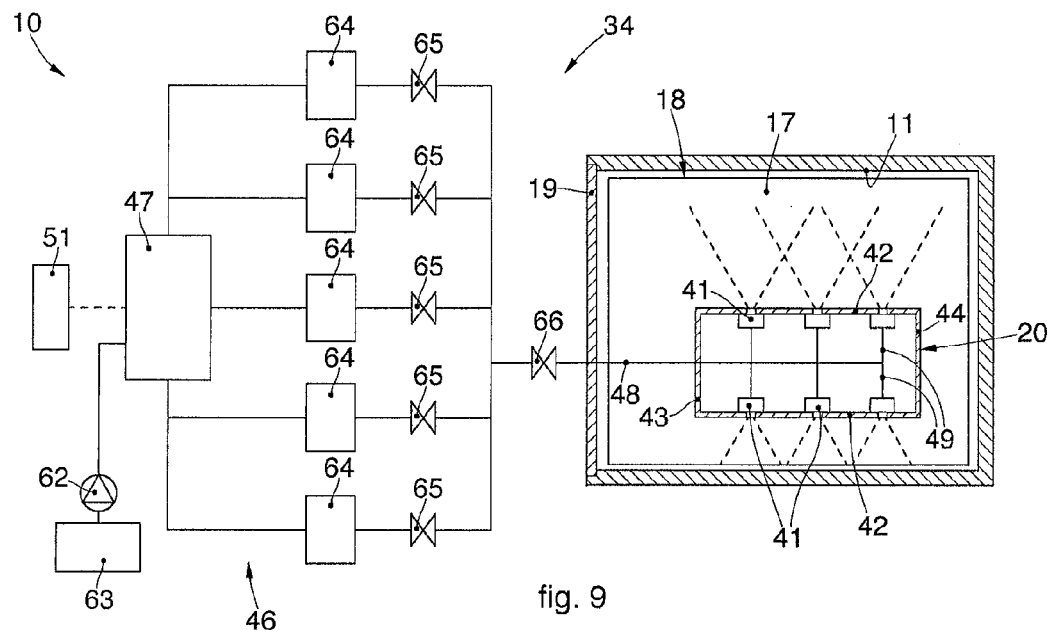
FIG. 9 is a schematic representation of a possible form of embodiment of the present invention.

FIG. 9 shows a diagram of a possible form of embodiment of the lyophilizing machine 10, in particular with reference to the distribution apparatus 46 to distribute the washing fluids.

FIG. 9 shows, on the left, the command module 51, connected to the distribution module 46, in turn having washing nozzles 41 housed in the internal compartment 45 of the internal horizontal guide 20 and configured to clean a loading plane 18 inside the treatment chamber 11.

The distribution apparatus 46 can include one or more supply members 62, for example a pump, a compressor or other hydraulic or pneumatic systems, configured to supply the washing fluids to the accumulation tank 47. The supply members 62, only one of which is shown schematically in FIG. 9, can be connected to the water system, to systems for the distribution of gaseous fluids, or to one or more stores 63 of washing fluids.

The accumulation tank 47 can be connected to a plurality of intermediate tanks 64, each configured to contain simultaneously a desired quantity of a corresponding washing fluid, for example the quantity needed to carry out a complete washing cycle.

Each intermediate tank 64 can be connected to the collector 48 to transfer its content into it. A selection valve 65, interposed between the corresponding intermediate tank 64 and the collector 48 and configured to prevent or selectively allow the passage to the collector 48 of the washing fluid contained in the intermediate tank 64, is associated with each intermediate tank 64.

In possible forms of embodiment of the present invention, each selection valve 65 can be commanded to open or close by the command module 51.

The opening of several selection valves 65 allows, where required, to mix an equal number of washing fluids in the collector 48 upstream of the washing nozzles 41.

It is clear that modifications and/or additions of parts may be made to the lyophilizing machine 10 as described heretofore, without departing from the field and scope of the present invention.

It is also clear that, although the present invention has been described with reference to some specific examples, a person of skill in the art shall certainly be able to achieve many other equivalent forms of lyophilizing machine, having the characteristics as set forth in the claims and hence all coming within the field of protection defined thereby.

The invention claimed is:

1. Lyophilizing and/or sterilizing machine, comprising:
   a treatment chamber,
   a plurality of loading planes having at least one loading surface, disposed inside said treatment chamber, one overlapping the other,
   vertical tie-rods configured to position the plurality of loading planes,
   a movement apparatus comprising a loading/unloading device configured to load containers onto and unload containers from the loading surface of said loading planes, the content of which is to be treated in said treatment chamber,
   horizontal guides comprising at least one internal horizontal guide inside said treatment chamber, said at least one internal horizontal guide being independent and autonomous from the loading planes and located in correspondence to a lateral portion of the loading planes and between said loading surface and said vertical tie-rods, wherein said loading/unloading device is mobile on said internal horizontal guide,
   washing means comprising one or more delivery devices of washing fluids configured to carry out the cleaning of at least said loading surface of at least one of said loading planes, said washing means being integrated and at least partly contained in the at least one internal horizontal guide,
   a distribution apparatus of said washing fluids cooperating with said one or more delivery devices, and
   a command module configured to control and/or manage the distribution apparatus.

2. Lyophilizing and/or sterilizing machine as in claim 1, wherein said at least one internal horizontal guide is positioned between the loading surface and at least one lateral portion cooperating with the vertical tie-rods, said lateral portion being part of said loading planes.

3. Lyophilizing and/or sterilizing machine as in claim 2, wherein said plurality of loading planes each include an opening extending therethrough, the opening disposed between the loading surface and the at least one lateral portion, and said at least one internal horizontal guide extending through the opening.

4. Lyophilizing and/or sterilizing machine as in claim 3, wherein said at least one internal horizontal guide includes a lifting device configured to move the at least one internal horizontal guide vertically within the treatment chamber.

5. Lyophilizing and/or sterilizing machine as in claim 1, wherein said delivery devices are seated to one or more walls of the respective internal horizontal guide.

6. Lyophilizing and/or sterilizing machine as in claim 5, wherein said delivery devices are fixed with relation to the walls of the respective internal horizontal guide to which they are applied.

7. Lyophilizing and/or sterilizing machine as in claim 1, wherein said delivery devices are retractable and configured to assume at least an inactive position inside the perimeter of said respective internal horizontal guide, and a work position at least partly outside said respective internal horizontal guide.

8. Lyophilizing and/or sterilizing machine as in claim 1, wherein said distribution apparatus comprises:
at least one accumulation tank, and
one or more distribution pipes coupled to the at least one accumulation tank and disposed at least partly inside said at least one internal horizontal guide feeding said delivery devices.

9. Lyophilizing and/or sterilizing machine as in claim 8, wherein said distribution apparatus comprises at least one collector, interposed between said accumulation tank and said distribution pipes, said distribution pipes branching off from said collector toward said delivery devices and being inclined vertically in a manner converging toward said collector.

10. Lyophilizing and/or sterilizing machine as in claim 8, wherein said distribution apparatus comprises at least a pumping device connected to said accumulation tank and configured to pick up and send the washing fluids contained in said accumulation tank to said delivery devices.

11. Lyophilizing and/or sterilizing machine as in claim 8, wherein said washing means further comprise interception and/or selection means, associated to said distribution apparatus and interposed between said accumulation tank and said treatment chamber, and configured to selectively isolate said treatment chamber hydraulically, or to allow the flow of washing fluids toward said delivery devices.

12. Lyophilizing and/or sterilizing machine as in claim 1, wherein said delivery devices are disposed along a longitudinal extension of the internal horizontal guide, in at least one row, wherein the delivery devices of said at least one row are configured to deliver said washing fluids toward at least one of either said loading surface and a lower surface of at least one loading plane.

13. Lyophilizing and/or sterilizing machine as in claim 1, further comprising a lifting device connected to said at least one internal horizontal guide and configured to position said internal horizontal guide vertically on each occasion.

14. Lyophilizing and/or sterilizing machine as in claim 1, wherein the upper surface of the at least one internal horizontal guide has at least one raceway segment which can be temporally associated in a univocal manner with movement means of said loading/unloading device, command and control means being provided at least for the command and/or control at least of said movement means of said loading/unloading device.

15. Lyophilizing and/or sterilizing machine as in claim 14, wherein said at least one internal horizontal guide is integrated with supply and/or signal transmission means comprising at least energy supply means cooperating with captation means of said energy on board said loading/unloading device in order to power the movement means and the command and control means.

16. Lyophilizing and/or sterilizing machine as in claim 15, wherein said at least one internal horizontal guide is integrated with supply and/or signal transmission means comprising at least means for transporting command and control signals cooperating with said command and control means of the loading/unloading device.

17. Lyophilizing and/or sterilizing machine as in claim 15, wherein said supply and/or signal transmission means are associated at least in a single conductor configured to supply the desired power and/or signals and information to the movement means and/or the command and control means present in the loading/unloading device.

18. Lyophilizing and/or sterilizing machine as in claim 15, wherein said supply and/or signal transmission means comprise a first electric conductor cooperating with said raceway to supply power to the movement means of the loading/unloading device and a second electric conductor, positioned inside said at least one internal horizontal guide, configured to transmit signals and information toward, and receive them from, the command and control means of said loading/unloading device.

19. Lyophilizing and/or sterilizing machine as in claim 1, wherein the at least one internal horizontal guide is fixedly coupled to the treatment chamber, and the vertical tie rods are configured to move one of the plurality of loading planes so that an upper surface of the internal horizontal guide is coplanar with the loading surface of the one of the plurality of loading planes in response to the loading/unloading device loading containers onto or unloading containers from the loading surface.

20. Lyophilizing and/or sterilizing machine as in claim 1, wherein the at least one internal horizontal guide has a box-shaped configuration with inwardly and outwardly facing walls and seatings disposed laterally along the inwardly and outwardly facing walls, and the delivery devices comprise nozzles mounted within the seatings in the inwardly and outwardly facings walls of the at least one internal horizontal guide.

* * * * *